US012702471B2

(12) United States Patent
Gershonowitz et al.

(10) Patent No.: US 12,702,471 B2
(45) **Date of Patent: *Aug. 11, 2026**

(54) DEVICES AND METHODS FOR FRACTIONAL TREATMENT OF TISSUE

(71) Applicant: POLLOGEN LTD., Tel Aviv (IL)

(72) Inventors: Amikam Gershonowitz, Tel Aviv (IL); Eyal Ben Esti, Tel Aviv (IL); Mordechai Moti Elnekave, Haifa (IL)

(73) Assignee: POLLOGEN LTD., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 19/330,315

(22) Filed: Sep. 16, 2025

(65) Prior Publication Data

US 2026/0020896 A1 Jan. 22, 2026

Related U.S. Application Data

(63) Continuation of application No. 19/035,520, filed on Jan. 23, 2025, which is a continuation of application
(Continued)

(51) Int. Cl.
*A61B 18/14* (2006.01)
*A61B 18/00* (2006.01)

(52) U.S. Cl.
CPC .... *A61B 18/14* (2013.01); *A61B 2018/00577* (2013.01); *A61B 2018/1425* (2013.01)

(58) Field of Classification Search
CPC ................ A61B 18/1477; A61B 18/14; A61B 2018/00577; A61B 2018/143;
(Continued)

(56) References Cited

U.S. PATENT DOCUMENTS 6,918,907 B2 * 7/2005 Kelly ................. A61B 18/1477 606/100
7,278,991 B2 * 10/2007 Morris ............... A61B 18/1477 606/41
(Continued)

FOREIGN PATENT DOCUMENTS

EP 3226796 10/2017

OTHER PUBLICATIONS

Search Report—corresponding PCT Application No. PCT/IL2024/050558, dated Jul. 31, 2024, 14 pages.

*Primary Examiner* — Michael F Peffley
(74) *Attorney, Agent, or Firm* — ISUS Intellectual Property PLLC; Anthony Jason Mirabito

(57) ABSTRACT

A tissue treatment device and method comprising a plurality of spaced-apart elongated electrodes configured to receive radio frequency (RF) signal from an RF energy source and for be inserted into tissue at a plurality of depths. The elongated electrodes having a first polarity and a single flat electrode located having a second polarity. The single flat electrode is located in vicinity of the elongated electrodes and configured for contacting the tissue surface and for receiving the RF signal from the RF energy source. An actuating mechanism connected to the plurality of elongated electrodes and configured to move the elongated electrodes in two opposite directions into and out of the tissue. A controller as part of the treatment device configured to apply fractional treatment to the tissue, vary spatial density of the fractional treatment over a treatment period, operate the actuating mechanism to selectively move different elongated electrode sub-groups of the plurality of elongated electrodes according to a treatment time pattern.

24 Claims, 7 Drawing Sheets

Related U.S. Application Data

No. 18/736,081, filed on Jun. 6, 2024, now Pat. No. 12,239,358.

(60) Provisional application No. 63/471,294, filed on Jun. 6, 2023.

(58) Field of Classification Search
CPC .... A61B 2018/1425; A61B 2018/1206; A61B 2018/0016; A61B 2018/126
See application file for complete search history.

(56) References Cited

U.S. PATENT DOCUMENTS

| | | | | |
|---|---|---|---|---|
| 2019/0099599 | A1* | 4/2019 | Kreindel | A61N 1/36 |
| 2021/0361343 | A1* | 11/2021 | Gershonowitz | A61B 18/14 |
| 2023/0085916 | A1* | 3/2023 | Kreindel | A61B 18/14 606/41 |

* cited by examiner

RF energy Source
150
Controller
140
130
100A
Actuating Mechanism
100
160
Impedance measurement
110
120
110B
110C
110A
120
12
t1
110T
D1
SD1
10H
10
110B
110C
110A
120
t2
SD1
D2
SD2

DEVICES AND METHODS FOR FRACTIONAL TREATMENT OF TISSUE

RELATED APPLICATIONS

This application is a continuation application of U.S. application Ser. No. 19/035,520, filed Jan. 23, 2025, which is a continuation application of U.S. application Ser. No. 18/736,081, filed Jun. 6, 2024, now U.S. Pat. No. 12,239,358, issued on Mar. 4, 2025, which is related to and claims priority to U.S. Provisional Application No. 63/471,294 filed Jun. 6, 2023, entitled "DEVICES AND METHODS FOR FRACTIONAL TREATMENT OF TISSUE," to which application priority is hereby claimed.

TECHNOLOGICAL FIELD

The present invention is in the medical aesthetic field and relates specifically to devices and methods for treatment of tissue, such as the skin, for aesthetic and/or cosmetic purposes. More specifically, the present disclosure relates to an apparatus for fractional treatment of skin tissue of a patient.

BACKGROUND

Various skin treatment techniques for skin rejuvenation are available. Some treatments involve fractional skin treatment, a term used to describe a form of treatment that creates a discrete array of relatively small treatment spots in the skin tissue and leaves sites of healthy and untreated tissue around the treatment spots. The treatment spots may be created by optical (e.g. laser), electromagnetic (e.g. radio frequency), sound (e.g. Ultrasound) or other energies/modalities. At each treatment spot a micro damage is created in the skin tissue. The micro damage in the skin tissue at the treatment spots initiates a natural healing response of the skin tissue. The intact healthy tissue surrounding the treatment spots provides basis for healing the micro damage.

Examples for fractional skin treatment can be found in WO2021234609A1 and WO2021234605A1 both assigned to the assignee of the present invention.

SUMMARY

The presently disclosed subject matter provides a technique for fractional treatment of tissue, using micro-electrodes for delivering electrical current, in particular an Alternating Current (AC) signal. Devices and methods are presented for effective fractional treatment by increasing treatment comfort and outcome. The micro-electrodes may be configured with elongated shapes enabling their insertion into deep layers of the tissue and optionally below the skin tissue into fat and/or muscle layers. To this end, herein below, the micro-electrodes have a length dimension being much larger than their width and depth dimensions and may be referred to as micro-needles to describe the functionality of deep insertion into the tissue.

In accordance with a first aspect of the presently disclosed subject matter, there is provided a tissue treatment device comprising: a plurality of spaced-apart elongated electrodes configured to receive radio frequency (RF) signal at a first polarity from an RF energy source, and be inserted into tissue at one or more depths; a single flat electrode located in vicinity of the elongated electrodes and configured to receive the RF signal from the RF energy source, at a second polarity being opposite to the first polarity, and contact a tissue surface; an actuating mechanism connected to the plurality of elongated electrodes and configured to move the plurality of elongated electrodes along a first axis, in two opposite directions into and out of the tissue; and a controller connected to the plurality of elongated electrodes, the flat electrode, the RF energy source, and the actuating mechanism configured to apply RF energy to the tissue, and actuate the actuating mechanism to insert and remove different RF needle sub-groups of the plurality of spaced-apart elongated electrodes into and out of the tissue to provide fractional treatment to the tissue selectively and variably.

In another aspect, the tissue treatment device, wherein said controller is configured to operate the RF energy source in an insertion phase and a subsequent treatment phase, the insertion phase comprises applying the RF signal to the plurality of elongated electrodes to cause ablation of the tissue in contact with distal ends of the elongated electrodes. The controller is further configured to vary spatial density of the fractional treatment over a treatment time period by operating the actuating mechanism to selectively move different elongated electrode sub-groups of the plurality of elongated electrodes according to a treatment time pattern. The spatial density is varied between a first distance and a second distance equaling $1/\sqrt{2}$ of the first distance.

In yet another aspect, the tissue treatment device, wherein said first distance is equal to 2.2 mm and wherein said plurality of elongated electrodes comprise a first array of elongated electrodes spaced-apart with a first distance and a second array of elongated electrodes spaced-apart with a second distance, the first and second arrays defining said different elongated electrode sub-groups. The tissue treatment device, wherein the first and second distances are equal and are 2.2 mm and said first array comprises a first number of elongated electrodes extending along a second axis and said second array comprises a second number of elongated electrodes extending along the second axis, the second number being smaller than the first number.

In yet another aspect, there is a tissue treatment device, wherein when each elongated electrode of the second array is inserted into the tissue is located equidistant to every four adjacent elongated electrodes of the first array and said actuating mechanism comprises a first actuating motor connected to the first array and a second actuating motor connected to the second array, the first and second actuating motors are independently controllable by the controller. Also, the tissue treatment device, wherein the elongated electrodes of said first array have an equal first length and the elongated electrodes of said second array have an equal second length and said first array of elongated electrodes is positioned over a first stage and said second array of elongated electrodes is positioned over a second stage, the first and second stages are movable with respect to each other, along the first axis, by said actuating mechanism.

In one aspect, there is a tissue treatment device, wherein said second stage is arranged behind the first stage along the first axis, the first stage comprising holes along the first axis enabling passage of the second array of elongated electrodes therethrough and said plurality of elongated electrodes have different lengths. The tissue treatment device wherein said one or more depths comprise a maximal depth of between 7-10 mm and at least some of the plurality of elongated electrodes have a flat body. The tissue treatment device, wherein the flat body of each electrode of said first array has a length of 3 mm and width and thickness of 100-200 μm each and the flat body of each electrode of said second array has a length of 7 mm and width and thickness of 200-300 μm each.

In another aspect, there is a tissue treatment device, wherein at least some of the plurality of elongated electrodes have at least one of: a curved body; a blunt distal end; a pointed distal end; different cross-sectional shapes; different cross-sectional areas; insulation along a proximal external surface thereof; or insulation along whole external surface except of a bottom side thereof.

In one aspect, there is a tissue treatment device, wherein at least some of the plurality of elongated electrodes are arranged in a plurality of comb-like one dimensional arrays and said flat electrode is perforated with holes through which the plurality of elongated electrodes is passed along the first axis. The tissue treatment device, further comprising: a main body configured to be held by a user, the main body housing the actuating mechanism and the controller; and a disposable tip removably connectable to the main body and housing the plurality of elongated electrodes and the flat electrode. The tissue treatment device, further comprising an RF energy source being housed within the main body.

In yet another aspect, tissue treatment device, wherein the controller is further configured to vary spatial density by actuating the mechanism as follows: a) during insertion phase, operate the RF energy source at a first RF signal profile that causes ablation of tissue contacting distal ends of the plurality of elongated electrodes, and operate the actuating mechanism to move the plurality of elongated electrodes into the tissue; b) during treatment phase, operate the RF energy source at a second RF signal profile that causes fractional treatment of tissue contacting the distal ends of the plurality of elongated electrodes, for a predetermined treatment period; and c) during disengagement phase, operate the actuating mechanism to move the plurality of elongated electrodes out of the tissue.

In one aspect, the tissue treatment device, wherein said controller is further configured to sequentially repeat said (a) and (b) operations for two or more times corresponding to different sub-groups of the plurality of elongated electrodes, to thereby vary spatial density of the treatment. The tissue treatment device wherein said controller is configured to operate the RF energy source at a third RF signal profile during the disengagement phase.

In another aspect, there is a method for fractional treatment of tissue, the method comprising:

- providing:
  - a plurality of elongated electrodes having a first polarity; and
  - a single flat electrode located in vicinity of the elongated electrodes and having a second polarity opposite the first polarity;
- placing:
  - the single flat electrode in contact with a tissue surface; and
  - tips of the plurality of elongated electrodes into contact with the tissue surface;
- supplying a first RF signal profile to the elongated electrodes and the single flat electrode;
- supplying, upon detecting a closed circuit between the plurality of elongated electrodes and the single flat electrode, a second RF signal profile adapted to cause ablation of the tissue in contact with the tips of the plurality of elongated electrodes;
- inserting, while supplying the second RF signal, different RF needle sub-groups of the plurality of elongated electrodes into the tissue selectively and variably, at predetermined rates corresponding to the ablation of the tissue, and for a predetermined insertion period until reaching a predetermined depth; and
- withdrawing the plurality of elongated electrodes out of the tissue.

In one aspect, the method further comprising repeating steps of supplying the first RF signal and the second RF signal and inserting the plurality of elongated electrodes before withdrawing the plurality of elongated electrodes. The method further comprising supplying, after the plurality of elongated electrodes reach the predetermined depth, and before withdrawing the plurality of elongated electrodes out of the tissue, a third RF signal profile configured to treat the tissue, for a predetermined treatment period, at the predetermined depth. The method further comprising measuring impedance of the tissue and determining the second RF signal profile based on the measured impedance. The method further comprising measuring impedance of the tissue and determining the third RF signal profile based on the measured impedance.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings.

DETAILED DESCRIPTION

Fractional treatment with elongated micro-electrodes (micro-needles) can be limited due to a variety of factors, such as the mechanical properties of the thin and elongated shapes of the micro-needles: the needle size and strength limit the spatial density and depth of the treatment. In some embodiments, effective treatment (comfort and outcome) is achieved through inserting the needles by heating and ablation instead of mechanical insertion force, and through varying spatial density of the fractional treatment over the treatment period.

The ability to achieve higher spatial density of fractional treatment, than utilizing typical traditional micro-needles, may be achieved by using lower energies (per electrode/needle) and/or higher temporal resolution of the fractional treatment, for a given thermal relaxation time (TRT) of the tissue, than typical traditional microneedles. In some embodiments, multi-pulse regime avoids bulk heating and treats certain conditions more effectively. In some embodiments, more efficient heating leads to expected results without over treating/burning the treated tissue.

An AC signal may be applied to the tissue through micro-electrodes, this may be a RF signal, that is, the frequency of the signal is in the RF region of the electromagnetic spectrum. However, this should not limit the invention as other regions of the electromagnetic spectrum may be applicable as well.

Figure 1A:
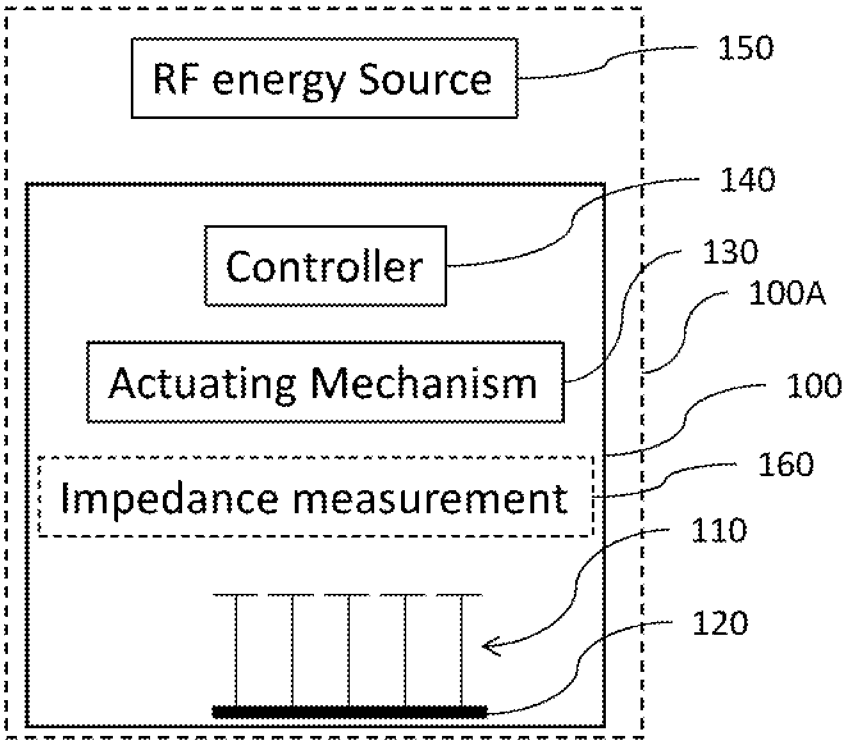
FIGS. 1A-1C illustrate a non-limiting exemplary embodiment of a device according to the invention.
Figure 1B:
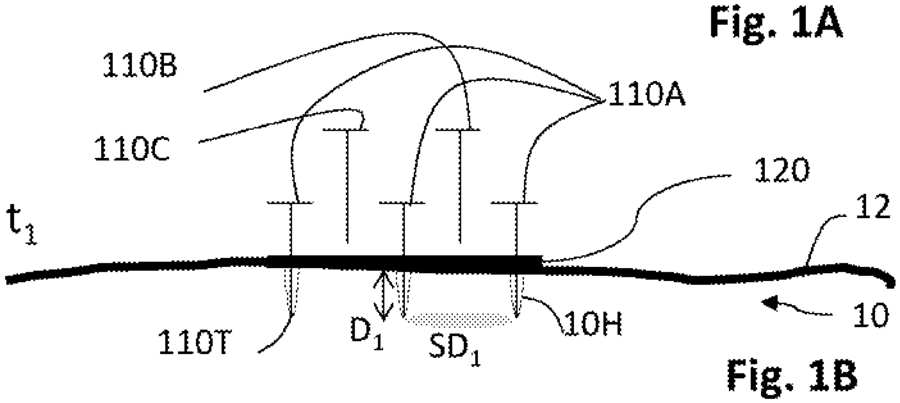
Figure 1C:
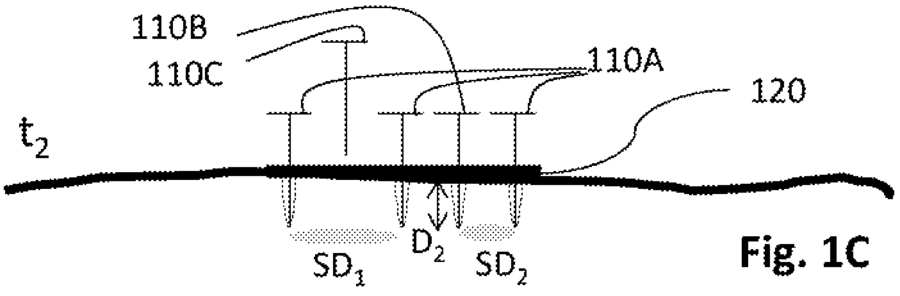

Reference is made to FIGS. 1A-1C illustrating, by way of a block diagram, a non-limiting example of a device 100 for fractional treatment of the tissue 10 (as used herein, the tissue specifically includes the skin and possibly additional tissue such as fat or muscle), in accordance with some non-limiting embodiments of the presently disclosed subject matter. As shown, the device 100 includes a plurality of spaced-apart micro-electrodes (micro-needle electrodes) 110, a single flat electrode 120, an actuating mechanism 130 and a controller 140. As described above, the specific non-limiting examples referred to herein may be called radio frequency (RF) electrodes.

The plurality of spaced-apart RF needle electrodes 110 are configured for receiving RF energy (signal) from an RF (AC) source 150 and for being inserted into the skin tissue to one or more depths. It is noted that while in the description herein, the exemplified electrical signal is AC, it can also be a DC (direct current) or a combination thereof. As may be appreciated from FIG. 1A, the RF energy source 150 does not form a part of the device 100, although in some embodiments, it can form part of a device 100A that includes the device 100 and the RF source 150, as illustrated by the dashed line in FIG. 1A. In some embodiments, the plurality of RF needle electrodes are arranged to form a one-dimensional array. In some embodiments, the plurality of RF needle electrodes are arranged to form a two-dimensional array. In some embodiments, the plurality of RF needle electrodes have equal lengths. In some embodiments, the plurality of RF needle electrodes have different lengths. In some embodiments, the plurality of RF needle electrodes are distanced with a fixed, equal, distance between every two adjacent needles. In some embodiments, the plurality of RF needle electrodes are distanced with a varied, inequal, distances between at least some of the needles.

The single flat RF electrode 120 is configured for contacting the surface 12 of the skin tissue 10 and for receiving the RF energy from the RF energy source. The plurality of RF needle electrodes 110 are configured to connect to a first pole of the RF energy source, thereby having a first polarity, and the flat RF electrode 120 is configured to connect to a second, opposite, pole of the RF energy source, thereby having a second polarity being opposite to the first polarity of the plurality of RF needle electrodes 110. It is to be understood that the first polarity of the RF needle electrodes 110 will be opposite to the second polarity of the flat RF electrode 120 at each given time, although the first and second polarities may be switching back and forth according to the frequency of the RF signal provided by the RF signal source 150.

In general, an arrangement of two electrodes works either in a mono-polar or a bi-polar activation mode. This is effected by two main factors, the current density and the physical distance. Typically, in the mono-polar mode, a first electrode and a second electrode produce different current densities (high against low) while being located far away from each other (e.g. a first small electrode (high current density) located at a finger of a subject and a second large electrode (low current density) located at the lower back of the subject). Typically, in the bi-polar mode, the first and second electrodes produce similar (specifically equal) current densities while being located in close proximity to each other.

In some embodiments, the plurality of RF elongated electrodes 110 and the single flat RF electrode 120 operate in a pseudo-mono-bi-polar (or duo-polar) mode as each of the plurality of elongated electrodes 110 produce a higher current density than the flat single RF electrode 120 (as in mono-polar mode) while the plurality of elongated electrodes 110 and the single flat electrode 120 are located in close proximity to each other.

Therefore, the device 100 may operate in a duo-polar mode such that each one of the plurality of RF needle electrodes operates against the single flat RF electrode 120. As the single flat RF electrode 120 has a surface area that is much larger than the surface of the tip 110T of each RF needle electrode, the RF current density at the needle tip is large enough resulting in very high temperature at the tissue in vicinity of the needle tip, and the very high temperature causes ablation of the tissue, as illustrated by the tissue holes 10H surrounding the inserted portions of the RF needle electrodes. Accordingly, the device 100 is configured for insertion of the plurality of RF needle electrodes into the tissue by tissue heating and ablation and without excessive insertion force.

In some embodiment, the plurality of RF needle electrodes and the single flat RF electrode should be located in close proximity to each other to enable the duo-polar mode. In some embodiments, the RF needle electrodes and flat RF electrode are located beside each other with respect to the skin surface. In some embodiments, the RF needle electrodes and flat RF electrode intersect with each other relative to the skin surface, e.g. the single flat RF electrode include holes through which the plurality of RF needle electrodes pass.

The actuating mechanism 130 is connected to the plurality of RF needle electrodes 110 and configured and operable to move the plurality of RF needle electrodes along a first axis, in two opposite directions into and out of the skin tissue 10. In some embodiments, the first axis is perpendicular to the skin surface 12. It is understood that the actuating mechanism can be configured and controlled to move the RF needle electrodes individually or in predefined groups as the treatment protocol dictates. In some embodiments, the actuating mechanism is configured to insert the plurality of RF needles to one or more depths inside the skin tissue and/or deeper into the fat and/or muscle tissues. In some embodiments, a maximal depth is determined by the length of at least some of the plurality of RF needle electrodes. In some embodiments, the maximal depth is about 7 mm.

The controller 140 is operatively connected to the plurality of RF needle electrodes, the flat electrode, the RF energy source and the actuating mechanism, for controlling and applying the fractional RF treatment to the skin tissue (and/or fat and/or muscle tissue). The controller is configured, inter alia, to control the RF energy parameters, such as the frequency and amplitude of the RF signal, the treatment time, the duty cycle the selection of activated RF needle electrodes, and the actuating mechanism responsible for progressing and retracting the activated RF needle electrodes towards and away from the skin tissue.

The controller 140 may be configured to operate the RF energy source 150 in an insertion phase and a subsequent treatment phase, the insertion phase comprises applying the RF energy to the plurality of RF needle electrodes and the flat electrode to cause ablation of the skin tissue in vicinity of the distal ends of the RF needle electrodes. Furthermore, the controller 140 may be configured to vary spatial density of the fractional RF treatment over a treatment time period by operating the actuating mechanism 130 to selectively move different RF needle sub-groups of the plurality of RF needle electrodes, according to a treatment time pattern.

A non-limiting example of varying the spatial density of the fractional RF treatment by the controller 140 is shown in FIGS. 1B and 1C. A user may decide the plurality of RF needle electrodes 110 should be divided, in this example, into three sub-groups: sub-group 110A including three RF needle electrodes, sub-group 110B including one RF needle electrode and sub-group 110C including one RF needle electrode.

At a first time period $t_1$, the controller 140 operates the RF energy source 150 and the actuating mechanism 130 to insert the sub-group 110A to a depth D1 and to apply a fractional treatment having a spatial density $SD_1$. For simplicity of presentation, it is assumed that the five RF needle electrodes 110 are placed in a row beside each other with a distance X between each two adjacent needle electrodes. Accordingly, the spatial density $SD_1$ corresponds to a distance 2X between each two adjacent needle electrodes of the sub-group 110A. At a second time period $t_2$, the controller 140 may operate the RF energy source 150 and the actuating mechanism 130 to insert the sub-group 110B to a depth D2 and to apply a fractional treatment with the sub-groups 110A and 110B. It is now appreciated that the fractional RF treatment has a spatial density $SD_1$ between the two RF needle electrodes of the sub-group 110A on the left side and a spatial density $SD_2$ between the three RF needle electrodes on the right (two of sub-group 110A and one of the sub-group 110B).

Accordingly, the spatial density of the fractional RF treatment may be varied along the treatment period. It is appreciated that the spatial density $SD_2$, in this non limiting example, is twice the spatial density $SD_1$. It is also appreciated that the depths $D_1$ and $D_2$ can be equal or different.

While the sub-group 110C, in this non-limiting example, is not activated, it is appreciated that it can be controlled by the controller 140 and inserted to a depth $D_3$ (not shown, equal to or different from $D_1$, $D_2$), such that the fractional RF treatment starts with the spatial density $SD_1$ and continues with the spatial density $SD_2$, across the whole treated skin tissue portion, or vice versa.

While not specifically shown, it can also be envisaged that at time period $t_3$, one or more of the sub-groups 110A-110C may be retracted/withdrawn out of the skin tissue to again alter the spatial density of the treatment or to end the treatment.

It is to be also noted that different sub-groups can be sequentially inserted and withdrawn during a treatment session. For example, a multi-step approach may be implemented, first inserting and withdrawing sub-group 110A/B/C, and only then inserting and withdrawing other sub-groups 110B/C/A.

In some embodiments, the device includes an impedance measurement device/circuit 160, configured to measure impedance of the tissue, during the treatment which includes inserting and withdrawing the RF needle electrodes 110 into and out of the tissue and applying the treatment at predetermined one or more depths. The impedance measurement is transmitted to the controller 140 that controls the RF signal accordingly to enable the insertion of the RF needle electrodes and the treatment.

In some embodiments, the impedance of the tissue is estimated based on depth into the tissue. For example, a look-up table of impedance values as function of depth may be utilized by the controller 140 to adapt the RF signal to the specific depth. In some embodiments, the impedance of the tissue is estimated based on the tissue type. In some embodiments, the impedance is estimated based on combination of depth and tissue type.

Figure 2A:
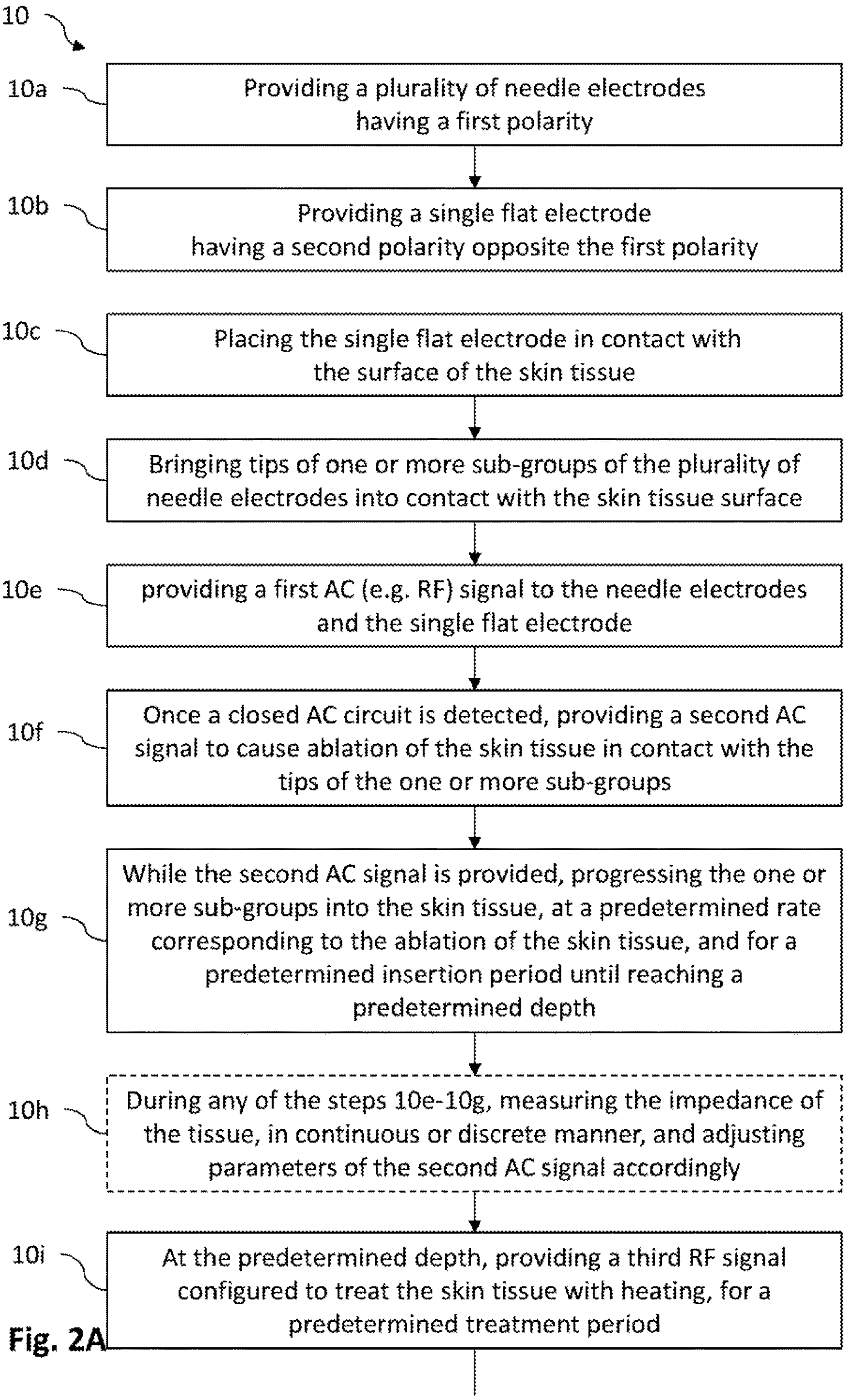
FIGS. 2A and 2B illustrates a non-limiting exemplary embodiment of a method according to the invention.
Figure 2B:
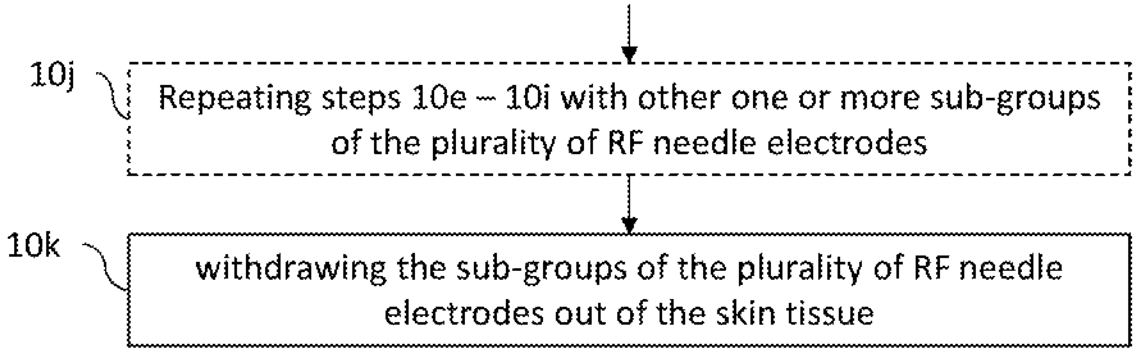

Reference is made to FIGS. 2A and 2B illustrating, by a flow chart, an example of a method 10 for applying a fractional treatment to a skin tissue, in accordance with some non-limiting embodiments of the present disclosure.

In step 10*a*, a plurality of elongated RF (needle) electrodes having a first polarity are provided.

In step 10*b*, a single flat RF electrode having a second polarity opposite the first polarity is provided.

In step 10*c*, the single flat electrode is placed in contact with the surface of the skin tissue.

In step 10*d*, tips of one or more sub-groups of the plurality of RF needle electrodes are brought into contact with the skin tissue surface.

In step 10*e*, a first RF signal to the RF needle electrodes and the single flat RF electrode is provided to confirm contact between the tips of the needle electrodes and the flat electrode and the tissue.

In step 10*f*, once a closed circuit is detected in step 10*e*, a second RF signal configured to cause ablation of the skin tissue in contact with the tips of the one or more sub-groups is provided. In some embodiments, the second RF signal may have a value in the range of 10-100W.

In step 10*g*, while the second RF signal is provided, the one or more sub-groups are progressed/inserted into the skin tissue, at a predetermined rate (speed) corresponding to the ablation of the skin tissue, and for a predetermined insertion period until reaching a predetermined depth. It can be appreciated that the second RF signal can be adjusted to apply a treatment simultaneously with the insertion or withdrawal of the needle electrodes.

In step 10*h*, during any of the steps 10*e*-10*g*, impedance of the tissue is measured, in continuous or discrete manner by the controller using a sensor, and parameters of the second RF signal are adjusted/adapted accordingly to enable the ablation and insertion of the needle RF electrodes and the treatment of the tissue. In some embodiments, other factors are considered to adjust/adapt the value/parameters of the second RF signal, such as depth, energy density (number of working needle electrodes), insertion speed, and tissue type. It is, for example, known that the outer layer (stratum corneum) of the skin tissue has a higher impedance than deeper skin tissue layers, thus requiring a second RF signal having a higher power profile when ablating the stratum corneum compared to that required to ablate the deeper tissue.

Therefore, it can be appreciated that the second RF signal may have a varying profile and divided into a penetrating pulse (one capable of ablating the stratum corneum) and a working pulse (one capable of ablating the deeper tissue layer(s), the working pulse will have a smaller magnitude than the penetrating pulse).

In step 10*i*, optionally a third RF signal configured to treat the skin tissue, at the predetermined depth, with heating, is provided for a predetermined treatment period. In some embodiments, the value/parameters of the third RF signal is determined based on impedance, depth, treatment period, energy density (number of working needle electrodes).

It is appreciated that steps 10*g*-10*i* may be sequentially repeated for a few times to apply fractional treatment to different depths within the skin tissue.

Optionally, in step 10*j*, steps 10*e*-10*i* are repeated with more one or more sub-groups of the plurality of RF needle electrodes, to apply fractional RF treatment, having varied spatial density, to the skin tissue.

In step 10*k*, the sub-groups of the plurality of RF needle electrodes that have been inserted (by ablation) into the skin tissue are withdrawn out of the skin tissue and the treatment is finished. It can be appreciated that the second and/or third RF signals may be also applied during the withdrawal of the needle electrodes. It can also be appreciated that the division above into first, second and third RF signals is recited for illustration and understanding, and alternatively there may be a merged single adaptive RF signal being adjusted through the different stages of contact detection, insertion by ablation, treatment and withdrawal of the needle electrodes.

It is appreciated that method 10 can be applied using the device described with reference to FIG. 1.

Figure 3A:
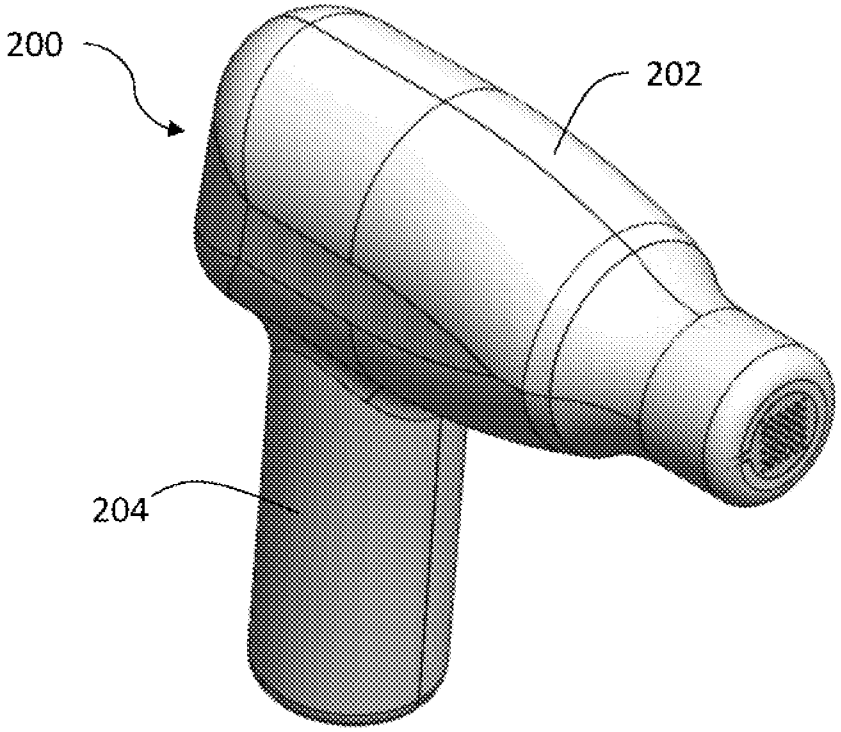
FIGS. 3A-3G illustrate another non-limiting exemplary embodiment of a device having two needle electrodes array, according to the invention.

Reference is made to FIGS. 3A-illustrating a non-limiting example of a device 200 configured in accordance with the present disclosure. Elements/features that have the same/similar function as described in FIGS. 1A-1C are referred to by numbers having one hundred difference. The device 200 has a housing/enclosure 202 configured to enclose the plurality of RF needle electrodes, the single flat electrode, the actuating mechanism and the controller. Optionally, the housing 202 also encloses the RF energy source therein. As shown in this non-limiting example, the housing 202 has a gun-like form and includes a handle 204 configured to be grasped by the user of the device.

Figure 3B:
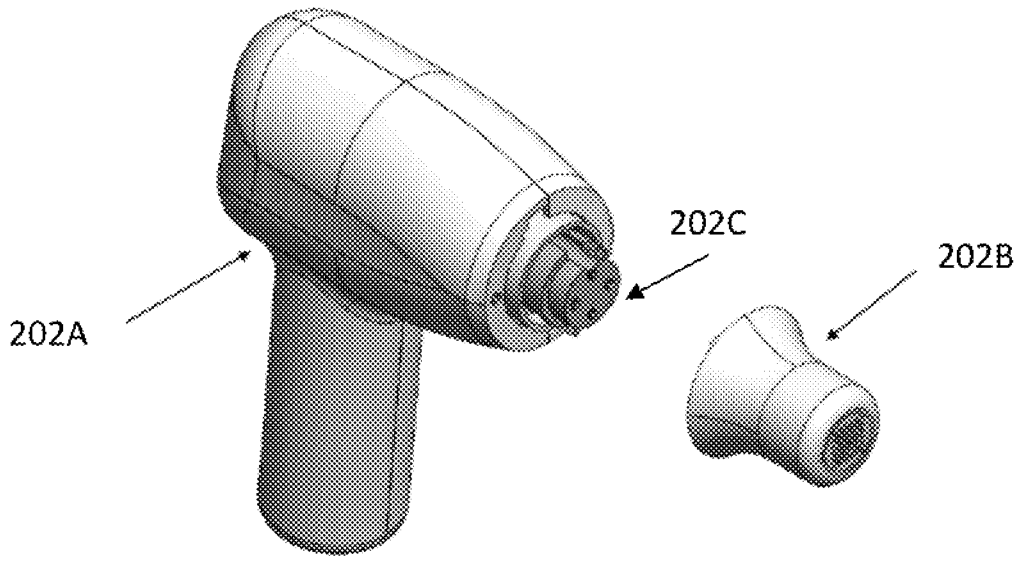

As shown in FIG. 3B, and in some embodiments, the housing of the device includes a main body 200A that includes the handle 204. As shown in FIG. 3G, the main body 202A houses the actuating mechanism 230 and the controller 240 that, in this example, is located within the handle 204. The housing also includes a disposable tip 202B removably connectable to the main body 202A and housing the plurality of RF needle electrodes and the flat RF electrode, as will be described further below. In some embodiments, a connector 202C that transmits the signals between the actuating mechanism and the controller, including the RF signals, to the plurality of RF needle electrodes and the flat RF electrode is located at the interface between the main body and the disposable tip. In one example, as shown, the connector 202C is in the form of Pogo pins.

Figure 3C:
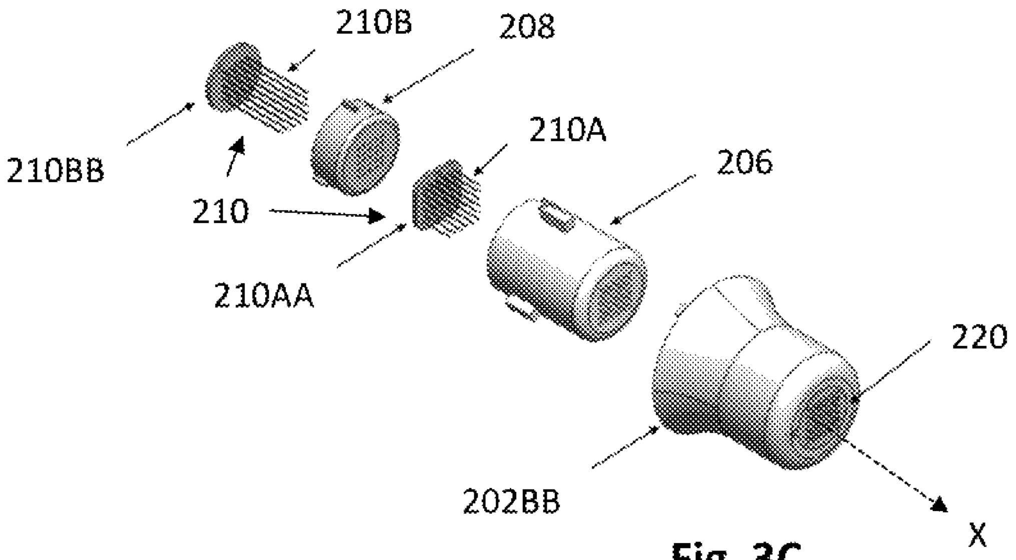
Figure 3D:
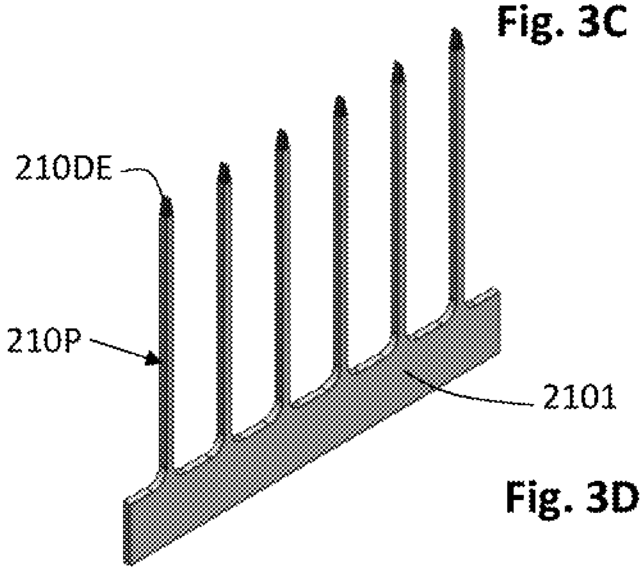
Figure 3E:
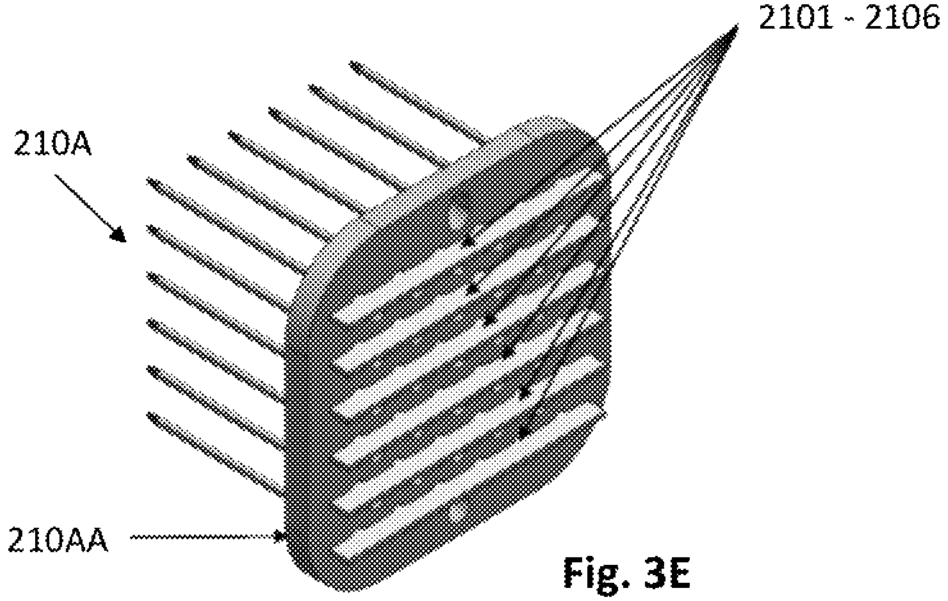
Figure 3F:
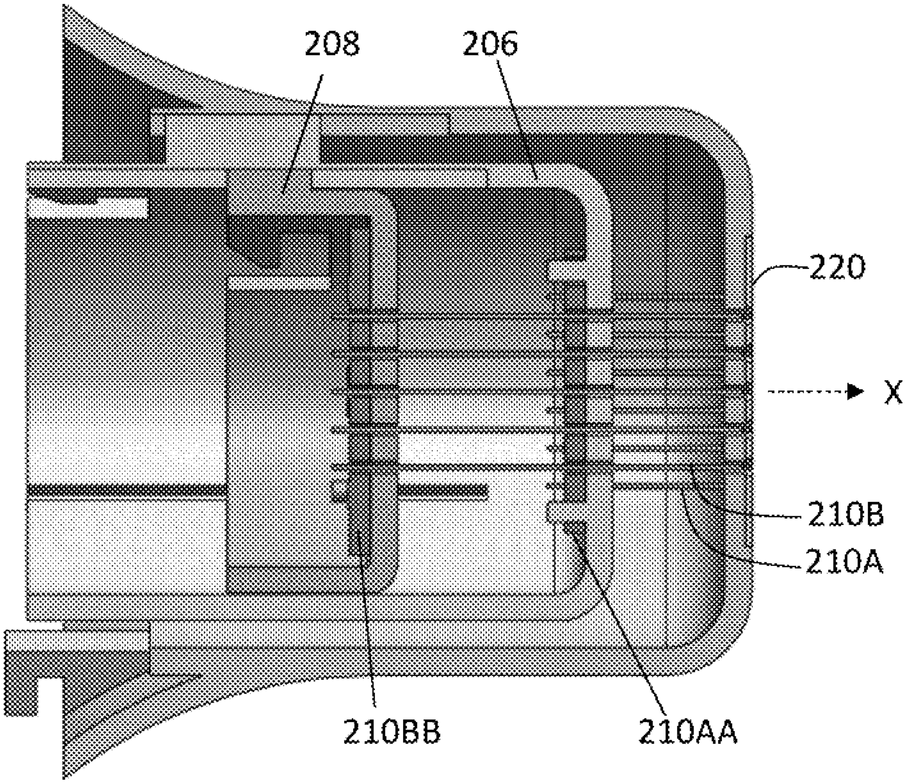
Figure 3G:
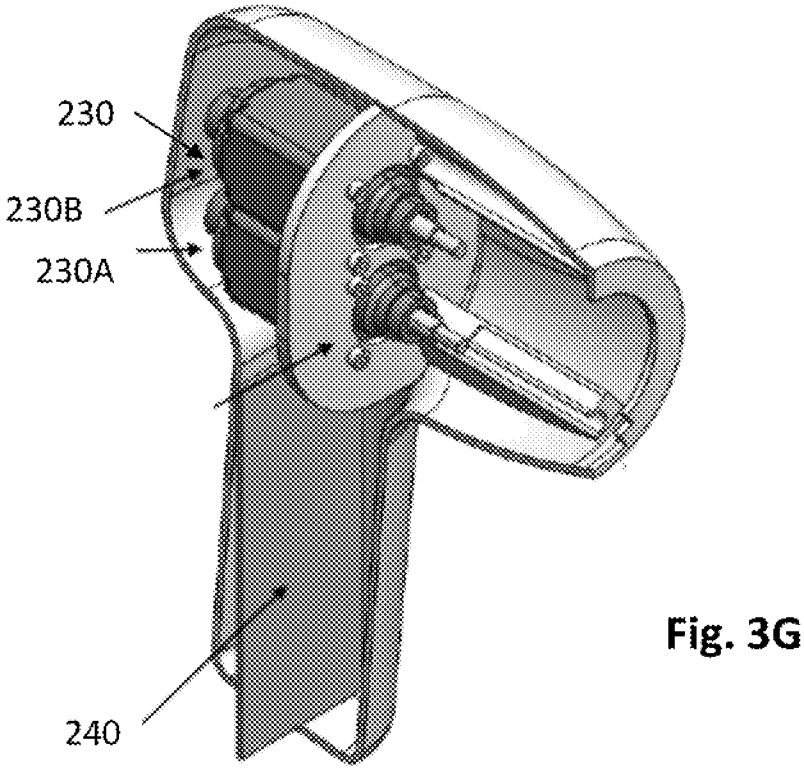

In FIG. 3C, an exploded view of the disposable tip 202B with the internal parts is shown, and in FIG. 3G a side sectional view of the assembled disposable tip is shown. At the distal end configured for touching and contacting the skin tissue, a single flat electrode 220 is located. The flat electrode 220 is perforated and has a plurality of holes corresponding to the plurality of RF needle electrodes, such that the latter pass through the holes towards the skin tissue.

The plurality of RF needle electrodes 210 include two sub-groups of needle electrodes, a first two-dimensional needle array 210A and a second two-dimensional needle array 210B, arranged in tandem one behind the other with respect to the axis X. The first array 210A is received within a guide 206 and the second array 210A is received within a guide 208, the guides 206 and 208 are connected to the actuating mechanism to enable movement of each guide and the respective needle array back and forth along the axis X.

In some embodiments, the first array includes a first number of RF needle electrodes extending along plane normal to axis X, and the second array includes a second number of RF needle electrodes extending along the plane. In some embodiments, the second number is smaller than the first number.

In some embodiments, the RF needle electrodes of the first array of are spaced-apart with a first distance and the RF needle electrodes of the second array are spaced-apart with a second distance. In some embodiments, the first and second distances determine the spatial density of the fractional treatment spots. In some embodiments, the first and second distances are equal. In some embodiments, the RF needle electrodes of the first array have an equal first length and the RF needle electrodes of said second array have an equal second length.

In this non-limiting example, the first array 210A includes 6×6 RF needles arranged at equal distances therebetween, and the second array 210B includes 5×5 RF needles arranged at equal distances therebetween such that each of the RF needles of the second array is located equidistant to every four RF needles of the first array. This way, if the distance between two adjacent RF needles of the first array is a, the distance between each two adjacent RF needles of the second array is also a, and the distance between each RF needle of the first array and the adjacent RF needle of the second array is $a/\sqrt{2}$. So, if the distance between the adjacent needles in each array is 2.2 mm, the spatial density of the RF treatment spots will vary between 2.2 mm, when only one of the first and second arrays is inserted into the skin tissue, and $2.2/\sqrt{2}$ mm, when both arrays are inserted.

As shown, and in some embodiments, the first array 210A is positioned over a first stage 210AA, and the second array 210B is positioned over a second stage 210BB, the first and second stages are movable with respect to each other, along the axis X, by the actuating mechanism 230. The first and second stage may also function as PCBs to electrically connect the RF needle electrodes to the controller 240 and to the RF energy source. As shown, in this example, the second stage 210BB is arranged behind the first stage 210AA along the axis X, the first stage 210AA has holes along the axis X to enable passage of the second array 210B therethrough.

In some embodiments, such as in this example in FIG. 3H, the actuating mechanism 230 includes a first actuating motor 230A connected to the first array 110A and a second actuating motor 230B connected to the second array 110B. In some embodiments, the first and second actuating motors are independently controllable by the controller 240, to independently move the first and second arrays in both directions along the axis X. The first and second actuating motors may be linear motors and can have a continuous movement mechanism or a stepped movement mechanism.

FIGS. 3D and 3E illustrate non-limiting examples of features of the RF needle electrodes that can be used with the device of the present disclosure. In some embodiments, some or all of the RF needle electrodes have a flat body, not rounded, that has a width and thickness. In some embodiments, the flat body has a width that is different than the thickness. In some embodiments, the width and the thickness are equal, e.g. in the range of 150 μm-250 μm. It is appreciated that the longer the needle, it can be made thicker to withstand the forces acting thereon.

In some embodiments, at least some of the RF needle electrodes have different cross-sectional shapes (e.g., circular, rectangular, polygonal). In some embodiments, at least some of the RF needle electrodes that have identical cross-sectional shapes, have different cross-sectional areas (e.g. a first group/array of needle electrodes has a circular shape with a first cross-sectional area and a second group/array of needle electrodes has a circular shape with a second cross sectional area different from the first cross sectional area).

As mentioned above, the RF needle electrodes are inserted by ablation and therefore, the needles need not have a sharp distal end for piercing the tissue. In some embodiments, some or all of the RF needle electrodes have a blunt distal end. In some embodiments, some or all of the RF needle electrodes have a pointed distal end that is not necessarily sharp. In some embodiments, some or all of the RF needle electrodes are insulated along a proximal external portion thereof, leaving only the distal end to be conductive when contacting the surrounding tissue. In some embodiments, some or all of the RF needle electrodes are insulated along their whole length (external surface) except only for the bottom side (face) which is conductive. The bottom face can be flat or can be curved. Complete insulation may insure, among other things, that the ablation is going along the progression movement and enables focused and controllably local fractional RF treatment at the selected depth(s).

In the illustrated example, the first array 110A is shown, having 6×6 needles that are insulated along the whole proximal length 210P of the needles except for the distal end 210DE with the conductive material exposed.

In some embodiments, the RF needle electrodes are arranged in a plurality of comb-like one dimensional arrays. This enhances the needles strength and facilitates their manufacturing. As shown in the present example, the first array 210A includes six comb-like needle arrays 2101-2106 arranged one beside the other to form the 6×6 two-dimensional array.

Reference is made to FIGS. 4A-4F illustrating non-limiting examples of the elongated micro-electrode configured in accordance with the present invention.

Figure 4A:
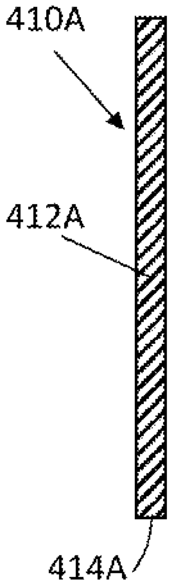
FIGS. 4A-4F illustrate various shapes for the elongated (needle) electrode used in the device, according to non-limiting embodiments of the present invention.
Figure 4B:
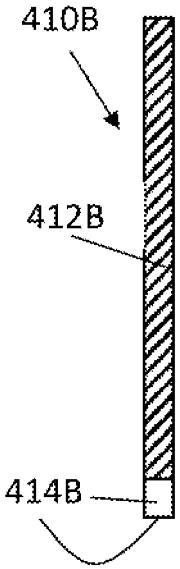

FIGS. 4A-4B are side views illustrating the insulation of the external surface of the needle electrode. FIG. 4A shows a preferred insulation profile 412A that extends for the whole length L of the elongated needle electrode 410A. The conductive part 414A is at the bottom side of the needle electrode. FIG. 4B shows another insulation profile 412B that extends for most part of the length of the elongated needle electrode 410B. The conductive part 414B extends along part of the length and bottom side of the needle electrode.

Figure 4C:

FIG. 4C illustrates a round (circular or oval) cross-section of the needle electrode, perpendicular to the length of the needle electrode.

Figure 4D:

FIG. 4D shows a rectangular cross-section of the needle electrode, perpendicular to the length of the needle electrode.

Figure 4E:
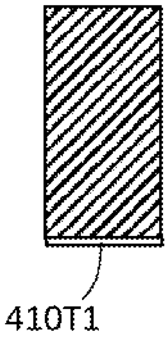

FIG. 4E illustrates a preferred flat tip 410T1 (having round or rectangular external shape), that can be fitted with either of the needle electrodes 410A and 410B. as described above, since no mechanical piercing is required, the tip can be flat.

Figure 4F:
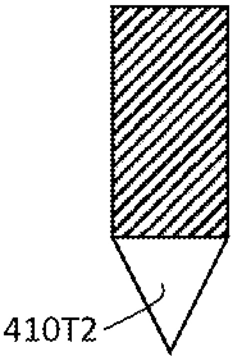

FIG. 4F shows a pyramidal or conical tip, that can be fitted with the needle electrodes 412A and 412B respectively.

It is noted and appreciated that other shapes for the insulation, the cross-section and the tip are possible within the scope of the present invention. Accordingly, the presently disclosed subject matter enables fractional treatment with variable spatial density, utilizing controlled insertion and withdrawal of sub-groups of needle electrodes into and out of the tissue. This enables less painful and more dense treatment resulting in better outcome.

The invention claimed is:

1. A tissue treatment device comprising:

a plurality of spaced-apart elongated electrodes configured to:

receive a radio frequency (RF) signal at a first polarity from an RF energy source; and be inserted into the tissue at one or more depths;

a single flat electrode located distally to the elongated electrodes on an axis X, the single flat electrode being perforated and having a plurality of holes corresponding to a positioning of the plurality of spaced-apart elongated electrodes, wherein the plurality of spaced-apart elongated electrodes are configured to pass through the holes towards the tissue, wherein the single flat electrode is configured to contact a tissue surface of the tissue and receive the RF signal from the RF energy source, at a second polarity being opposite to the first polarity;

wherein a first plurality of the plurality of the spaced apart elongated electrodes is mounted as a first planar array on a first stage positioned proximally of the single flat electrode along the axis X, the first array of elongated electrodes being oriented distally of the first stage;

wherein a second plurality of the plurality of spaced apart elongated electrodes is mounted as a second planar array on a second stage positioned proximally of the first stage along the X axis, the second plurality of elongated electrodes being oriented distally of the second stage;

the first stage further comprising a second plurality of holes among the spaced apart elongated electrodes of the first stage corresponding to the plurality of spaced apart electrodes of the second stage along the axis X to enable passage therethrough of elongated electrodes of the second stage through the second plurality of holes in the first stage;

the elongated electrodes of the first stage and the elongated electrodes of the second stage being oriented along the X axis so as to pass through the plurality of holes in the single flat electrode;

an actuator connected to the first and second stages and configured to selectively and independently move the plurality of elongated electrodes in the first stage and in the second stage along the axis X, in two opposite directions through the plurality of holes in the single flat electrode into and out of the tissue; and a controller connected to the plurality of elongated electrodes on the first stage and on the second stage, the flat electrode, the RF energy source, and the actuator configured to:

apply RF energy to the tissue; and actuate the actuator to selectively and independently insert and remove the first and second plurality of elongated electrodes into and out of the tissue, to different depths into the tissue, to provide fractional treatment to the tissue in multiple depths.

2. The tissue treatment device according to claim 1, wherein the controller is configured to operate the RF energy source in an insertion phase and a subsequent treatment phase, the insertion phase comprises applying the RF signal to the plurality of elongated electrodes on the first and second stages to cause ablation of the tissue in contact with the distal ends of the elongated electrodes, wherein the ablation caused by the RF signal in the insertion phase is sufficient to insert the elongated electrodes into tissue without mechanical insertion force.

3. The tissue treatment device according to claim 1, wherein the controller is further configured to vary spatial density of the fractional treatment over a treatment time period by operating the actuating mechanism to selectively and independently move the plurality of elongated electrodes in first and the second stages.

4. The tissue treatment device according to claim 3, where said spatial density is varied between a first distance between each two adjacent spaced-apart elongated electrodes and a second distance between each two adjacent spaced-apart elongated electrodes equaling $1/\sqrt{2}$ of the first distance.

5. The tissue treatment device according to claim 4, wherein said first distance is equal to 2.2 mm.

6. The tissue treatment device according to claim 4, wherein said first and second distances are equal.

7. The tissue treatment device according to claim 6, wherein said first and second distances are equal to 2.2 mm.

8. The tissue treatment device according to claim 1, wherein, when each elongated electrode of the second array is inserted into the tissue, each elongated electrode is located equidistant to every four adjacent elongated electrodes of the first array.

9. The tissue treatment device according to claim 1, wherein said actuator comprises a first actuating motor connected to the first array and a second actuating motor connected to the second array, the first and second actuating motors being independently controllable by the controller.

10. The tissue treatment device according to claim 1, wherein the elongated electrodes of said first planar array have an equal first length and the elongated electrodes of said second planar array have an equal second length.

11. The tissue treatment device according to claim 1, wherein said plurality of elongated electrodes have different lengths.

12. The tissue treatment device according to claim 1, wherein said one or more depths comprise a maximal depth of between 7-10 mm.

13. The tissue treatment device according to claim 1, wherein at least some of the plurality of elongated electrodes have a flat body.

14. The tissue treatment device according to claim 13, wherein the flat body of each electrode of said first array has a length of 3 mm and width and thickness of 100-200 μm each.

15. The tissue treatment device according to claim 13, wherein the flat body of each electrode of said second array has a length of 7 mm and width and thickness of 200-300 μm each.

16. The tissue treatment device according to claim 1, wherein at least some of the plurality of elongated electrodes have at least one of:

- a curved body;
- a blunt distal end;
- a pointed distal end;
- different cross-sectional shapes;
- different cross-sectional areas;
- insulation along a proximal external surface thereof; or
- insulation along whole external surface except of a bottom side thereof.

17. The tissue treatment device according to claim 1, wherein at least some of the plurality of elongated electrodes are arranged in a plurality of comb-like one dimensional arrays.

18. The tissue treatment device according to claim 1, comprising:

- a main body configured to be held by a user, the main body housing the actuator and the controller; and
- a disposable tip removably connectable to the main body and housing the plurality of elongated electrodes and the flat electrode.

19. The tissue treatment device according to claim 18, further comprising an RF energy source being housed within the main body.

20. The tissue treatment device according to claim 19, wherein the controller is further configured to vary spatial density by actuating the mechanism as follows:

a) during insertion phase, operate the RF energy source at a first RF signal profile that causes ablation of tissue contacting distal ends of the plurality of elongated electrodes, and operate the actuating mechanism to move the plurality of elongated electrodes into the tissue;

b) during treatment phase, operate the RF energy source at a second RF signal profile that causes treatment of tissue contacting the distal ends of the plurality of elongated electrodes, for a predetermined treatment period; and c) during disengagement phase, operate the actuating mechanism to move the plurality of elongated electrodes out of the tissue.

21. The tissue treatment device according to claim 20, wherein said controller is further configured to sequentially repeat said (a) and (b) operations for two or more times corresponding to the at least two different sub-groups of the plurality of elongated electrodes, to thereby vary spatial density of the treatment.

22. The tissue treatment device according to claim 20, wherein said controller is configured to operate the RF energy source at a third RF signal profile during the disengagement phase.

23. A method for fractional treatment of tissue, the method comprising:

- providing a plurality of spaced-apart elongated electrodes configured to: receive a radio frequency (RF) signal at a first polarity from an RF energy source and be inserted into the tissue at one or more depths;
- providing a single flat electrode located distally to the elongated electrodes on an axis X, the single flat electrode being perforated and having a plurality of holes corresponding to the positioning of the plurality of spaced-apart elongated electrodes, wherein the plurality of spaced-apart elongated electrodes are configured to pass through the holes towards the tissue, wherein the single flat electrode is configured to contact a tissue surface of the tissue and receive the RF signal from the RF energy source at a second polarity being opposite to the first polarity;
- wherein a first plurality of the plurality of the spaced apart elongated electrodes is mounted as a first planar array on a first stage positioned proximally of the single flat electrode along the axis X, the first array of elongated electrodes being oriented distally of the first stage;
- wherein a second plurality of the plurality of spaced apart elongated electrodes is mounted as a second planar array on a second stage positioned proximally of the first stage along the X axis, the second plurality of elongated electrodes being oriented distally of the second stage;
- wherein the first stage further comprises a second plurality of holes among the spaced apart elongated electrodes of the first stage corresponding to the plurality of spaced apart electrodes of the second stage along the axis X to enable passage therethrough of the elongated electrodes of the second stage through the second plurality of holes in the first stage;
- wherein the plurality of elongated electrodes of the first stage and the plurality of elongated electrodes of the second stage are oriented along the X axis so as to pass through the holes in the single flat electrode;
- wherein an actuator is connected to the first and second stages and configured to selectively and independently move the plurality of elongated electrodes in the first stage and the second stage along the axis X, in two opposite directions through the plurality of holes in the single flat electrode into and out of the tissue; and, wherein a controller is connected to the plurality of elongated electrodes on the first stage and the second stage, the flat electrode, the RF energy source, and the actuator;

the method further comprising, under control of the controller:

placing the single flat electrode in contact with a tissue surface and the tips of the plurality of elongated electrodes into contact with the tissue surface, through the plurality of holes of the single flat electrode;

applying RF energy to the tissue, wherein the applying comprises applying the RF signal to the elongated electrodes at the first polarity and to the single flat electrode at the second opposite polarity; and, inserting and removing, by the actuator, while supplying the RF signal, the elongated electrodes on the first stage and on the second stage into and out of the tissue at different depths into the tissue selectively and independently to provide fractional treatment to the tissue in multiple depths.

24. The method according to claim 23, further comprising:

measuring impedance of the tissue; and determining the RF signal based on the measured impedance.

* * * * *